United States Patent [19]

Petersen et al.

[11] Patent Number: 5,371,090
[45] Date of Patent: Dec. 6, 1994

[54] NAPHTHYRIDONECARBOXYLIC ACID DERIVATIVES

[75] Inventors: Uwe Petersen, Leverkusen; Andreas Krebs, Odenthal-Holz; Thomas Schenke, Bergisch Gladbach; Klaus Grohe, Odenthal; Klaus-Dieter Bremm, Dortmund; Rainer Endermann, Wuppertal; Karl-Georg Metzger, Wuppertal; Hans-Joachim Zeiler, Wuppertal, all of Germany

[73] Assignee: Bayer Aktiengesellschaft, Leverkusen, Germany

[21] Appl. No.: 199,371

[22] Filed: Feb. 18, 1994

Related U.S. Application Data

[62] Division of Ser. No. 901,056, Jun. 19, 1992, Pat. No. 5,312,823.

[30] Foreign Application Priority Data

Jun. 27, 1991 [DE] Germany .................. 4121214

[51] Int. Cl.5 .................. C07D 471/02; A61K 31/44
[52] U.S. Cl. .................. 514/300; 546/123
[58] Field of Search .................. 546/123; 514/300

[56] References Cited

FOREIGN PATENT DOCUMENTS

| 0047005 | 3/1982 | European Pat. Off. . |
|---|---|---|
| 0131839 | 1/1985 | European Pat. Off. . |
| 0153580 | 9/1985 | European Pat. Off. . |
| 0154780 | 9/1985 | European Pat. Off. . |
| 0321191 | 6/1989 | European Pat. Off. . |
| 0343560 | 11/1989 | European Pat. Off. . |
| 0424850 | 5/1991 | European Pat. Off. . |
| 0424851 | 5/1991 | European Pat. Off. . |
| 520277 | 12/1992 | European Pat. Off. . |
| 550903 | 7/1993 | European Pat. Off. . |
| 3420743 | 12/1985 | Germany . |
| 9313091 | 7/1993 | WIPO . |

OTHER PUBLICATIONS

Tetrahedron, vol. 39, No. 18, pp. 2869 to 2939, 1983.
Tetrahedron, vol. 45, No. 20, pp. 6519 to 6530, 1989.
Synthesis, Mar. 1979, pp. 221–223.
Tetrahedron Letters, No. 38, pp. 3291–3294, 1970.
Houben–Weyl, Bd. E4, pp. 144–149, 1983.
J.F.W. McOmie, Protective Groups in Org. Chemistry (1973), p. 43.
J. Org. Chem., vol. 38, No. 11, 1973, pp. 2049–2052.
Chemical Abstracts Service; CA 115:114488 of EP 424850 2 May 1991.
Chemical Abstracts Service; CA 115:114487 of EP 424852 2 May 1991.

*Primary Examiner*—Johann Richter
*Assistant Examiner*—Catherine S. Kilby Scalzo
*Attorney, Agent, or Firm*—Sprung Horn Kramer & Woods

[57] ABSTRACT

The invention relates to naphthyridonecarboxylic acid derivatives which are substituted in the 7-position by an optionally partially hydrogenated azaisoindolinyl ring, to processes for their preparation, and to antibacterial agents and feed additives containing them.

8 Claims, No Drawings

NAPHTHYRIDONECARBOXYLIC ACID DERIVATIVES

This is a division of application Ser. No. 07/901,056, filed Jun. 19, 1992 now U.S. Pat. No. 5,312,823.

The invention relates to new quinolone- and naphthyridonecarboxylic acid derivatives which are substituted in the 7-position by an optionally partially hydrogenated azaisoindolinyl ring, to processes for their preparation, and to antibacterial agents and feed additives containing them.

EP 343,560 has already disclosed quinolone- and naphthyridonecarboxylic acids which are substituted in the 7-position by an isoindolinyl ring such as, for example, 7-(2-isoindolinyl)-1-cyclopropyl-6,8-difluoro-1, 4-dihydro-4-oxo-3-quinolinecarboxylic acid. Moreover, EP 424,850 has disclosed 1-cyclopropyl-6,8-difluoro-7-(3, 8-diazabicyclo[4.3.0]non-1(6)-en-8-yl)-1,4-dihydro-4-oxo-quinolinecarboxylic acid, and EP 424,851 has disclosed 9-fluoro-3(S)-methyl-10-(3,8-diazabicyclo-[4.3.0]non-1(6)-en-8-yl)-7-oxo-2,3-dihydro-7H-pyrido[1,2,3-de][1,4]benzoxazine-6-carboxylic acid. However, the antibacterial activity of these compounds is incomplete.

It has been found that the compounds of the formula (I)

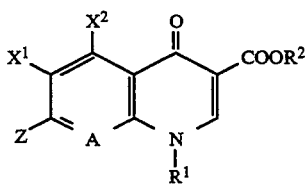

in which
- $X^1$ represents halogen,
- $X^2$ represents hydrogen, amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms, arylthio, halogen or methyl,
- $R^1$ represents alkyl having 1 to 4 carbon atoms, alkenyl having 2 to 4 carbon atoms, cycloalkyl having 3 to 6 carbon atoms, 2-hydroxyethyl, 2-fluoroethyl, methoxy, amino, methylamino, ethylamino, dimethylamino, or phenyl which is optionally substituted by 1 or 2 fluorine atoms,
- $R^2$ represents hydrogen, or represents alkyl which has 1 to 4 carbon atoms and which is optionally substituted by hydroxyl, methoxy, amino, methylamino or dimethylamino, or represents (5-methyl-2-oxo-1, 3-dioxol-4-yl)-methyl,
- Z represents a radical of the structure

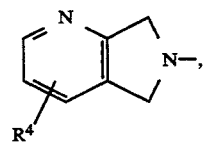

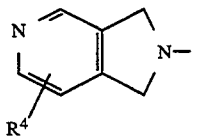

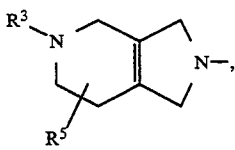

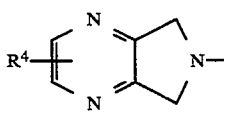

where
- $R^3$ represents hydrogen, optionally hydroxyl-substituted $C_1$-$C_3$-alkyl, alkoxycarbonyl having 1 to 4 C atoms in the alkoxy moiety or $C_1$-$C_3$-acyl,
- $R^4$ represents hydrogen, hydroxyl,

hydroxymethyl or

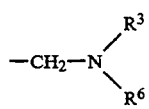

where
- $R^6$ denotes hydrogen or methyl,
- $R^5$ represents hydrogen, $C_1$-$C_3$-alkyl or cyclopropyl and
- A represents N or C—$R^7$ where
- $R^7$ represents H, halogen, methyl, hydroxyl or methoxy, or, alternatively, together with $R^1$ can form a bridge of the structure

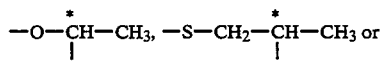

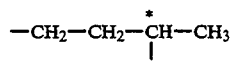

with the proviso that A cannot be N, CH or CF and cannot form with $R^1$ a bridge of the structure

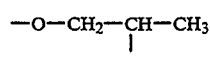

when
Z represents

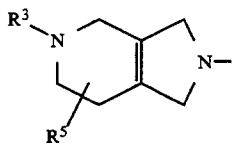

and their pharmaceutically usable hydrates and acid addition salts, and the alkali metal salts, alkaline earth metal salts, silver salts and guanidinium salts of the carboxylic acids on which they are based, have a higher antibacterial action compared with the prior art, in particular in the Gram-positive range.

Preferred compounds of the formula (I) are those in which $X^1$ represents fluorine, $X^2$ represents hydrogen, amino, methylamino, hydroxyl, methoxy, fluorine, chlorine, bromine or methyl, $R^1$ represents alkyl having 1 to 3 carbon atoms, vinyl, cycloalkyl having 3 to 4 carbon atoms, 2-fluoroethyl, or phenyl which is optionally substituted by 1 or 2 fluorine atoms, $R^2$ represents hydrogen, or represents alkyl which has 1 to 2 carbon atoms and is optionally substituted by amino, methylamino or dimethylamino, or represents (5-methyl-2-oxo-1,3-dioxol-4-yl)-methyl, Z represents a radical of the structure

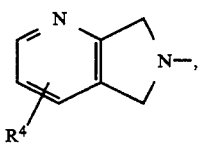

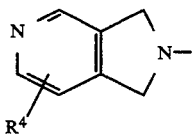

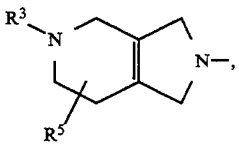

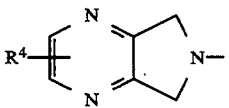

where $R^3$ represents hydrogen, optionally hydroxyl-substituted $C_1$-$C_2$-alkyl, alkoxycarbonyl having 1 to 4 C atoms in the alkoxy moiety or $C_1$-$C_3$-acyl, $R^4$ represents hydrogen, hydroxyl or

where $R^6$ denotes hydrogen or methyl, $R^5$ represents hydrogen or methyl and

A represents N or C—$R^7$ where $R^7$ represents H, fluorine, chlorine, bromine, methyl or methoxy or, alternatively, together with $R^1$ can form a bridge of the structure $$-O-CH_2-\overset{*}{C}H-CH_3,$$

with the proviso that A cannot be N, CH or CF and cannot form with $R^1$ a bridge of the structure $$-O-CH_2-CH-CH_3$$
$$\phantom{-O-CH_2-C}|$$

when

Z represents

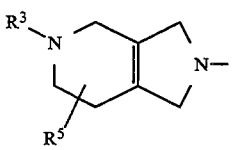

and their pharmaceutically usable hydrates and acid addition salts and the alkali metal salts, alkaline earth metal salts, silver salts and guanidinium salts of the carboxylic acids on which they are based.

Particularly preferred compounds of the formula (I) are those in which $X^1$ represents fluorine, $X^2$ represents hydrogen, amino, fluorine or bromine, $R^1$ represents alkyl having 1 to 2 carbon atoms, cyclopropyl, or phenyl which is optionally substituted by 1 or 2 fluorine atoms, $R^2$ represents hydrogen or alkyl having 1 to 2 carbon atoms, Z represents a radical of the structure

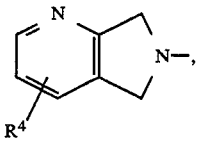

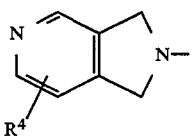

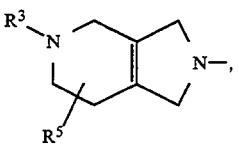

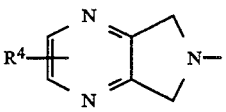

where
R³ represents hydrogen, methyl, alkoxycarbonyl having 1 to 4 C atoms in the alkoxy moiety, or C₁-C₃-acyl,
R⁴ represents hydrogen, hydroxyl or $$-N\begin{matrix}R^3\\R^6\end{matrix},$$

where
R⁶ denotes hydrogen or methyl,
R⁵ represents hydrogen or methyl and
A represents N or C—R⁷ where
R⁷ represents H, fluorine, chlorine or methoxy, or, alternatively, together with R¹ can form a bridge of the structure $$-O-CH_2-\overset{*}{C}H-CH_3,$$

with the proviso that A cannot be N, CH or CF and cannot form with R¹ a bridge of the structure $$-O-CH_2-\overset{}{C}H-CH_3$$

when
Z represents

[structure with R³-N, R⁵, and N-]

and their pharmaceutically usable hydrates and acid addition salts and the alkali metal salts, alkaline earth metal salts, silver salts and guanidinium salts of the carboxylic acids on which they are based.

Furthermore, it has been found that the compounds of the formula (I) are obtained when a compound of the formula (II)

[structure (II) with X¹, X², X³, COOR², N, R¹]

in which
A, R¹, R², X¹ and X² have the abovementioned meaning and
X³ represents halogen, in particular fluorine or chlorine,
are reacted with compounds of the formula (III)

Z—H                                                              (III)

in which
Z has the abovementioned meaning,
if appropriate in the presence of acid scavengers.

If, for example, 8-chloro-1-cyclopropyl-6,7-difluoro-1,4-dihydro-4-oxo-3-quinolinecarboxylic acid and 5-methyl-2,3,4,5,6,7-hexahydro-1H-pyrrolo[3,4-c]pyridine are used as starting substances, the course of the reaction can be represented by the following equation:

[reaction scheme]

Most of the compounds of the formula (II) which are used as starting substances are known or can be prepared by known methods. Examples which may be mentioned are:

7-chloro-1-cyclopropyl-6-fluoro-1,4-dihydro-4-oxo-3-quinolinecarboxylic acid (German Patent Application 3,142,854), 1-cyclopropyl-6,7-difluoro-1,4-dihydro-4-oxo-3-quinolinecarboxylic acid (European Patent Application 113,091), 6-chloro-1-cyclopropyl-7,8-difluoro-1,4-dihydro-4-oxo-3-quinolinecarboxylic acid (German Patent Application 3,420,743), 8-chloro-1-cyclopropyl-6,7-difluoro-1,4-dihydro-4-oxo-3-quinolinecarboxylic acid (German Patent Application 3,420,743), 1-cyclopropyl-6,7,8-trifluoro-1,4-dihydro-4-oxo-3-quinolinecarboxylic acid (German Patent Application 3,318,145), 5-bromo-1-cyclopropyl-6,7,8-trifluoro-1,4-dihydro-4-oxo-3-quinolinecarboxylic acid, 5-bromo-1-(2,4-difluorophenyl)-6,7,8-trifluoro-1,4-dihydro-4-oxo-3-quinolinecarboxylic acid, 1-cyclopropyl-6,7-difluoro-1,4-dihydro-8-methyl-4-oxo-3-quinolinecarboxylic acid, 6,7-difluoro-1-ethyl-1,4-dihydro-4-oxo-3-quinolinecarboxylic acid, 7-chloro-6-fluoro-1-ethyl-1,4-dihydro-4-oxo-3-quinolinecarboxylic acid, 7-chloro-6-fluoro-1,4-dihydro-1-(2-hydroxyethyl)-4-oxo-3-quinolinecarboxylic acid, 6,7-difluoro-1-(2-fluoroethyl)-1,4-dihydro-4-oxo-3-quinolinecarboxylic acid, 7-chloro-6-fluoro-1,4-dihydro-1-methoxy-4-oxo-3-quinolinecarboxylic acid, 7-chloro-6-fluoro-1,4-dihydro-1-methylamino-4-oxo-3-quinolinecarboxylic acid, 6,7-difluoro-1,4-dihydro-4-oxo-1-phenyl-3-quinolinecarboxylic acid, 7-chloro-1-cyclopropyl-6-fluoro-1,4-dihydro-4-oxo-1,8-naphthyridine-3-carboxylic acid, ethyl 7-chloro-1-cyclopropyl-6-fluoro-1,4-dihydro-4-oxo-1,8-naphthyridine-3-carboxylate, ethyl 1-cyclopropyl-6,7,8-trifluoro-1,4-dihydro-4-oxo-3quinolinecarboxylate (German Patent Application 3,318,145), 9,10-difluoro-2,3-dihydro-3-methyl-7-oxo-7H-pyrido-[1,2,3-de][1,4]benzoxacine-6-carboxylic acid (European Patent Application 47,005), 8,9-difluoro-6,7-dihydro-5-methyl-1-oxo-1H,5H-benzo[i,j]-quinolicine-2-carboxylic acid, 7-chloro-6-fluoro-1-phenyl-1,4-dihydro-4-oxo-1,8-naphthyridine-3-carboxylic acid (European Patent Application 153,580), ethyl 7-chloro-6-fluoro-1-(4-fluorophenyl)-1,4-dihydro-4-oxo-1, 8-naphthyridine-3-carboxylate, 6,7,8-trifluoro-1,4-dihydro-1-methylamino-4-oxo-3-quinolinecarboxylic acid (German Patent Application 3,409,922), 1-amino-6,7,8-trifluoro-1,4-dihydro-4-oxo-3-quinolinecarboxylic acid (German Patent Application 3,409,922), 6,7,8-trifluoro-1,4-dihydro-1-dimethylamino-4-oxo-3-quinolinecarboxylic acid (German Patent Application 3,409,922), 6,7-difluoro-1-(4-fluorophenyl)-1,4-dihydro-8-methyl-4-oxo-3-quinolinecarboxylic acid, 7-chloro-6-fluoro-1-(4-fluorophenyl)-1,4-dihydro-4-oxo-3-quinolinecarboxylic acid (European Patent Application 131,839), 7-chloro-6-fluoro-1-(2,4-difluorophenyl)-1,4-dihydro-4-oxo-3-quinolinecarboxylic acid (European Patent Application 131,839), 6,7,8-trifluoro-1-(4-fluorophenyl)-1,4-dihydro-4-oxo-3-quinolinecarboxylic acid (European Patent Application 154,780), 6,7,8-trifluoro-1-(2,4-difluorophenyl)-1,4-dihydro-4-oxo-3-quinolinecarboxylic acid (European Patent Application 154,780), 6,7,8-trifluoro-1,4-dihydro-4-oxo-1-phenyl-3-quinolinecarboxylic acid (European Patent Application 154,780), 7-chloro-1-ethyl-6-fluoro-1,4-dihydro-4-oxo-1,8-naphthyridine-3-carboxylic acid, 6,7-difluoro-1,4-dihydro-4-oxo-1-vinyl-3-quinolinecarboxylic acid, 1-cyclopropyl-5,6,7,8-tetrafluoro-1,4-dihydro-4-oxo-3-quinolinecarboxylic acid, 5-amino-1-cyclopropyl-6,7,8-trifluoro-1,4-dihydro-4-oxo-3-quinolinecarboxylic acid, 1-cyclopropyl-6,7,8-trifluoro-1,4-dihydro-5-hydroxy-4-oxo-3-quinolinecarboxylic acid, 1-cyclopropyl-6,7-difluoro-1,4-dihydro-8-methoxy-4-oxo-3-quinolinecarboxylic acid, 7-chloro-1-(2,4-difluorophenyl)-6-fluoro-1,4-dihydro-4-oxo-1,8-naphthyridine-3-carboxylic acid, ethyl 7-chloro-1-(2,4-difluorophenyl)-6-fluoro-1,4-dihydro-4-oxo-1, 8-naphthyridine-3-carboxylate.

Some of the bicyclic amines of the formula (III) which are required as starting substances are new. They can be prepared by the following processes.

1) N-Propargylurethane can be alkylated with 5- or 2-chloromethylpyrimidine or chloromethylpyrazine in the presence of strong bases. The subsequent intramolecular hetero-Diels-Alder reaction is effected either thermally or proton-catalysed [Tetrahedron 45, 6519 (1989)].

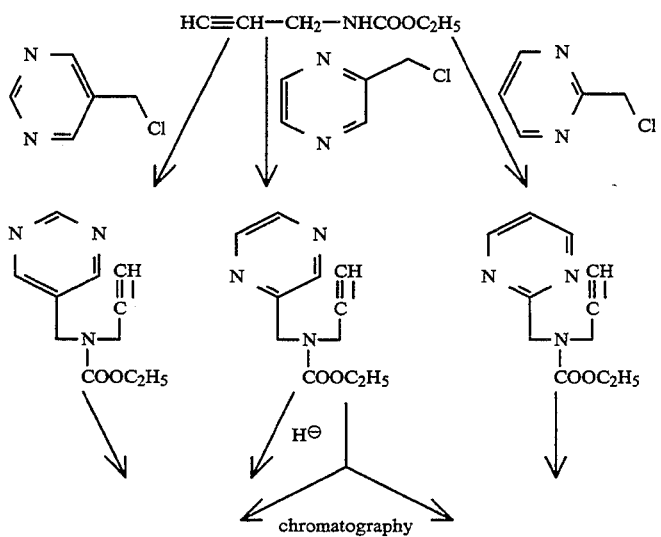

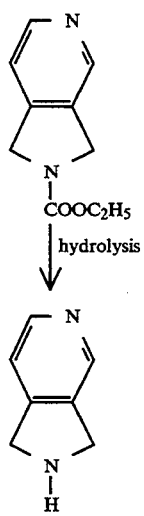

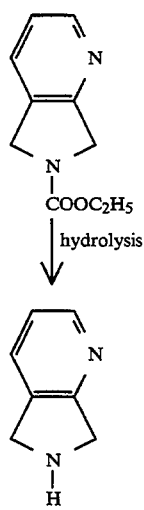

The intermediates of the N-propargyl-N-pyrazinyl-methylurethanes, or N-propargyl-N-(2-pyrimidinyl-methyl)urethanes and N-propargyl-N-(5-pyrimidinyl-methyl)urethanes can also be obtained by acylating aminomethylpyrazine, 2-aminomethylpyrimidine or 5-aminomethylpyrimidine with chloroformic esters, followed by alkylation with propargyl halides.

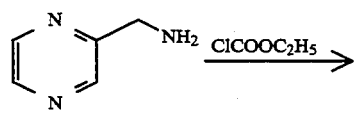

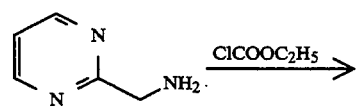

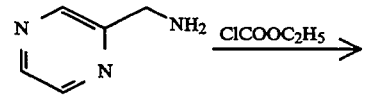

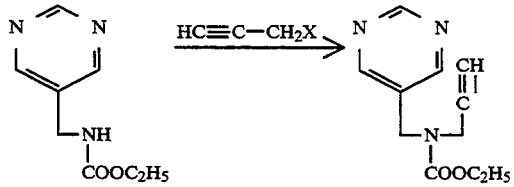

2) The enamines which can be prepared from the known pyrrolidin-3-ones by standard processes can be reacted with 1,2,4-triazine in a hetero-Diels-Alder reaction [Tetrahedron 39, 2869 (1983)].

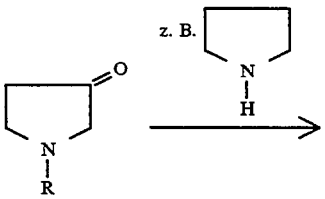

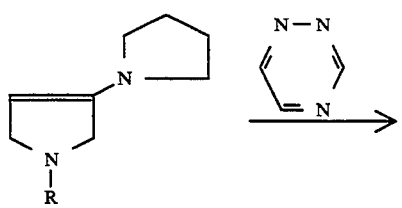

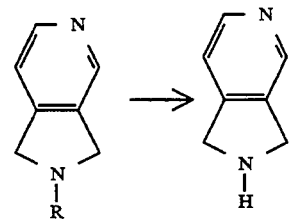

R = acyl, benzyl

3) Pyrrolidin-3-ones can also be converted into the O-allyl oxime ethers which can be rearranged by heating to give the pyridine derivatives [Synthesis 1979, 221]:

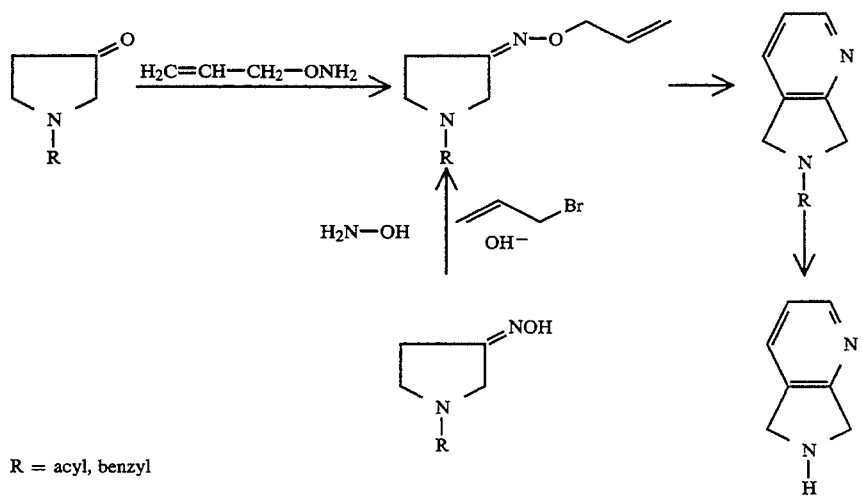

R = acyl, benzyl

4) Pyrrolidin-3-ones can also be reacted with 3-amino-acrolein to give the pyridine derivatives (Tetrahedron Lett. 1970, 3291).

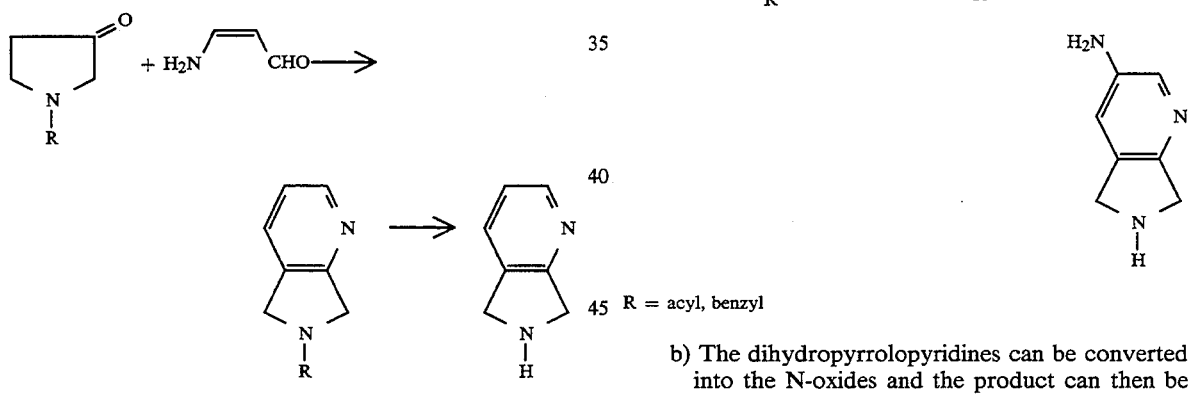

R = acyl, benzyl

5) Amino-substituted dihydropyrrolopyridines can be obtained by reduction of the corresponding nitro compounds, which are accessible via different routes:
   a) The enamines of the pyrrolidin-3-ones known from the literature can undergo a hetero-Diels-Alder reaction with 5-nitropyrimidine [Tetrahedron 39, 2869 (1983)].

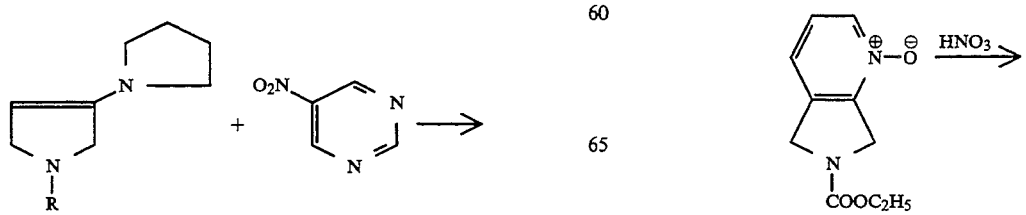

R = acyl, benzyl b) The dihydropyrrolopyridines can be converted into the N-oxides and the product can then be nitrated.

-continued

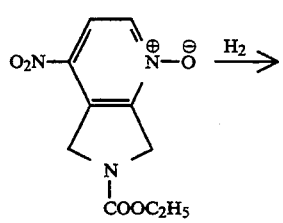

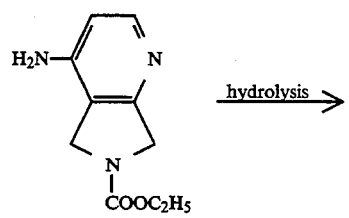

The resulting amino compounds can be monoalkylated or dialkylated on the amino group by generally known methods.

6) The corresponding hexahydro derivatives can be prepared by alkylation of the dihydropyrrolopyridines and reduction of the resulting pyridinium salts with sodium borohydride:

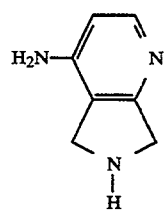

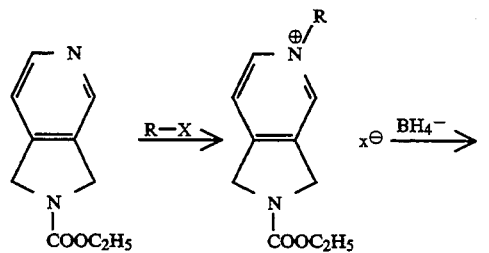

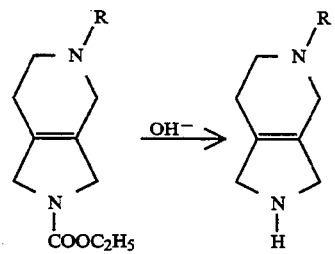

R = alkyl, X = halogen, sulphonate 7) 2,3-Bis-(chloromethyl)-pyrazine [Synthesis, 676 (1984)] can be reacted with benzylamine or amides to give 2,3-dihydro-1H-pyrrolo[3,4-b]pyrazine. The benzyl protective group can be dehydrogenated, and the acyl protective groups can be eliminated by acid or basic hydrolysis.

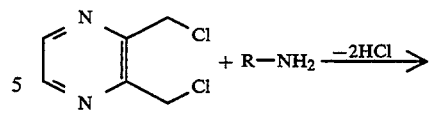

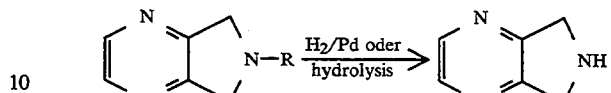

R = benzyl, acyl

The following may be mentioned as examples of compounds of the formula (III):

2,3,4,5,6,7-hexahydro-1H-pyrrolo[3,4-c]pyridine,
5-methyl-2,3,4,5,6,7-hexahydro-1H-pyrrolo[3,4-c]pyridine,
5-ethyl-2,3,4,5,6,7-hexahydro-1H-pyrrolo[3,4-c]pyridine,
5-(2-hydroxyethyl)-2,3,4,5,6,7-hexahydro-1H-pyrrolo-[3,4-c]pyridine,
5-(tert.-butoxycarbonyl)-2,3,4,5,6,7-hexahydro-1H-pyrrolo-[3,4-c]pyridine,
2,3-dihydro-1H-pyrrolo[3,4-b]pyrazine.

The reaction of (II) with (III), in which the compounds (III) can also be employed in the form of their salts such as, for example, the hydrochlorides, is preferably carried out in a diluent such as dimethyl sulphoxide, N,N-dimethylformamide, N-methylpyrrolidone, hexamethylphosphoric triamide, sulpholane, acetonitrile, water, an alcohol such as methanol, ethanol, n-propanol, isopropanol, glycol monomethyl ether or pyridine. Mixtures of these diluents can also be used.

Acid binders which can be used are all customary inorganic and organic acid-binding agents. These preferably include the alkali metal hydroxides, alkali metal carbonates, organic amines and amidines. The following particularly suitable substances may be mentioned individually: triethylamine, 1,4-diazabicyclo[2.2.2]octane (DABCO), 1,8-diazabicyclo[5.4.0]undec-7-ene (DBU) or excess amine (III).

The reaction temperatures can be varied within a substantial range. In general, the process is carried out between approx. 20° and 200° C., preferably between 80° and 180° C.

The reaction can be carried out under atmospheric pressure, but also under increased pressure. In general, the reaction is carried out at pressures between approx. 1 and 100 bar, preferably between 1 and 10 bar.

When carrying out the process according to the invention, 1 to 15 moles, preferably 1 to 6 moles, of the compound (III) are employed per mole of the compound (II).

Free amino groups can be protected during the reaction by a suitable amino protective group, for example the tert.-butoxycarbonyl radical, or as an azomethine group, and freed again after the reaction has ended by treatment with a suitable acid such as hydrochloric acid or trifluoroacetic acid (see Houben-Weyl, Methoden der Organischen Chemie [Methods in Organic Chemistry], Volume E4, page 144 (1983); J. F. W. McOmie, Protective Groups in Organic Chemistry (1973), page 43).

To prepare the esters according to the invention, the carboxylic acid on which they are based are preferably reacted in an excess of alcohol in the presence of strong acids such as sulphuric acid, anhydrous hydrogen chloride, methanesulphonic acid, p-toluenesulphonic acid or acid ion exchangers, at temperatures from approx. 20° to 200° C., preferably approx. 60° to 120° C. The water of reaction which forms can also be removed by azeotropic distillation with chloroform, tetrachloromethane, benzene or toluene.

Esters are also advantageously prepared by heating the acid on which they are based together with dimethylformamide dialkyl acetate in a solvent such as dimethylformamide.

The 5-methyl-2-oxo-1,3-dioxol-4-yl-methyl esters which are used as prodrugs are obtained by reacting an alkali metal salt of the carboxylic acid on which they are based and which can optionally be protected on the N atom by a protective group such as the tert.-butoxycarbonyl radical, with 4-bromomethyl- or 4-chloromethyl-5-methyl-1,3-dioxol-2-one in a solvent such as dimethylformamide, dimethylacetamide, N-methylpyrrolidone, dimethyl sulphoxide or tetramethylurea, at temperatures of approx. 0° to 100° C., preferably 0° to 50° C.

The acid addition salts of the compounds according to the invention are prepared in the customary manner, for example by dissolving the betaine in an excess of aqueous acid and precipitating the salt with a water-miscible organic solvent such as methanol, ethanol, acetone or acetonitrile. It is also possible to heat equivalent amounts of betaine and acid in water or an alcohol such as glycol monomethyl ether and subsequently evaporate the mixture to dryness, or filter off the precipitated salt by suction. Pharmaceutically usable salts are, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid.

The alkali metal salts or alkaline earth metal salts of the carboxylic acids according to the invention are obtained, for example, by dissolving the betaine in a substoichiometric amount of an aqueous solution of alkali metal hydroxide or alkaline earth metal hydroxide, filtration of undissolved betaine and evaporation of the filtrate to dryness. Sodium salts, potassium salts or calcium salts are suitable for pharmaceuticals. The corresponding silver salts are obtained by reacting an alkali metal salt or alkaline earth metal salt with a suitable silver salt such as silver nitrate.

In addition to the active compounds mentioned in the examples, the active compounds listed in the table below can also be prepared:

| $R^1$ | $R^2$ | $X^2$ | Z | A |
|---|---|---|---|---|
| cyclopropyl | H | H | pyrazinyl-N | C—OCH$_3$ |
| cyclopropyl | H | H | pyrazinyl-N | CF |
| cyclopropyl | H | H | pyrazinyl-N | CH |
| cyclopropyl | H | H | pyrazinyl-N | CCl |
| cyclopropyl | H | H | pyrazinyl-N | N |
| cyclopropyl | H | NH$_2$ | pyrazinyl-N | CF |

-continued
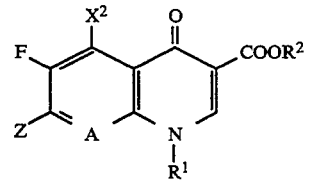
| R¹ | R² | X² | Z | A |
|---|---|---|---|---|
| 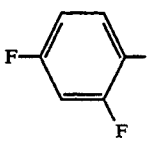 | H | H | 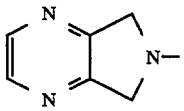 | N |
| (CH₃)₃C— | H | H | 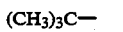 | CH |
| 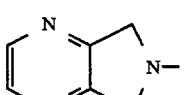 | H | H |  | CCl |
| 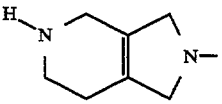 | H | H |  | CCl |
| 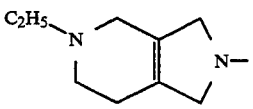 | H | Cl |  | CCl |
| 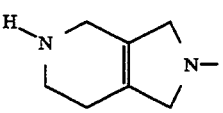 | H | Cl |  | CCl |
| 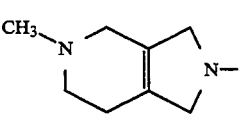 | H | H |  | C—CH₃ |
| 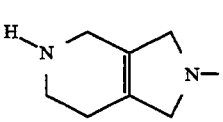 | H | H |  | C—CH₃ |
| 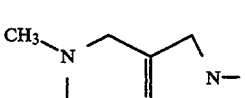 | H | H |  | CCl |
| 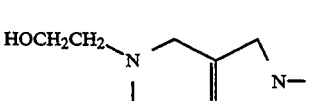 | H | H |  | CCl |
| 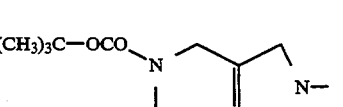 | H | H |  | CF |

-continued

| R¹ | R² | X² | Z | A |
|---|---|---|---|---|
| cyclopropyl | H | H | 4-amino-pyrido-pyrrolidine (NH₂-substituted) | CF |
| 2,4-difluorophenyl | H | H | N-methyl-octahydropyrrolo-pyridine | CCl |
| cyclopropyl | —CH₂CH₂NH₂ | H | N-methyl-octahydropyrrolo-pyridine | CCl |
| cyclopropyl | H | H | N-methyl-octahydropyrrolo-pyridine | OCH₃ |

The compounds according to the invention have a powerful antibiotic action and, while having a low toxicity, display a broad antibacterial spectrum against Gram-positive and Gram-negative germs, in particular against enterobacteria; mainly against those which are resistant to various antibiotics such as, for example, penicillins, cephalosporins, aminoglycosides, sulphonamides and tetracyclins.

These valuable properties allow them to be used in medicine as chemotherapeutic active substances and as preservatives of inorganic and organic materials, in particular a wide range of organic materials, for example polymers, lubricants, colouring substances, fibres, leather, paper and wood, foodstuffs and water.

The compounds according to the invention are active against a very broad range of microorganisms. It is possible, with their aid, to control Gram-negative and Gram-positive bacteria and bacteria-like microorganisms, and to prevent, alleviate and/or cure the diseases caused by these pathogens.

The compounds according to the invention are particularly active against bacteria and bacteria-like microorganisms. They are therefore particularly suitable for the prophylaxis and chemotherapy of local and systemic infections in human and veterinary medicine, caused by these pathogens.

The compounds are furthermore suitable for controlling diseases caused by Protozoa and Helminthes.

The compounds according to the invention can be used in various pharmaceutical preparations. Preferred pharmaceutical preparations which may be mentioned are tablets, coated tablets, capsules, pills, granules, suppositories, solutions, suspensions and emulsions, pastes, ointments, gels, creams, lotions, powders and sprays.

The minimum inhibitory concentrations (MICs) were determined on Iso-Sensitest agar (Oxoid) using serial dilution methods. For each test substance a series of agar plates was prepared which contained concentrations of the active substance which decreased as the dilution factor was doubled. The agar plates were inoculated by means of a multipoint inoculator (Denley). The inocula used were overnight cultures of the pathogens which had previously been diluted to such an extent that each inoculation point contained approx. $10^4$ colony-forming units. The inoculated agar plates were incubated at 37° C., and the growth of the germs was read off after approx. 20 hours. The MIC value ($\mu$g/ml) indicates the lowest concentration of active compound at which no growth could be observed with the naked eye.

The table below lists the MIC values of some of the compounds according to the invention compared with 7-(4-amino-1,3-dihydro-isoindol-2-yl)-1-cyclopropyl-6,8-difluoro-1,4-dihydro-4-oxo-3-quinolinecarboxylic acid (EP 343,560, Example 2).

TABLE

| Test strain: | Example | 1B | 2 | 3 | 5 | 6 | 4 | 7B | 8 | 9 | Ref.* |
|---|---|---|---|---|---|---|---|---|---|---|---|
| E. coli | Neumann | 0.13 | 0.06 | 0.13 | 0.13 | 0.13 | 0.06 | 0.02 | 0.03 | 0.25 | 0.5 |
|  | 455/7 | 8 | 8 | 128 | 128 | 128 | 128 | 2 | 1 | 128 | 128 |
| Klebsiella | 8085 | 0.25 | 0.13 | 0.5 | 1 | 0.5 | 0.25 | 0.06 | 0.06 | 0.5 | 4 |

| Test strain: | Example | 1B | 2 | 3 | 5 | 6 | 4 | 7B | 8 | 9 | Ref.* |
|---|---|---|---|---|---|---|---|---|---|---|---|
| sp. | | | | | | | | | | | |
| *Morganella morg.* | 932 | 0.13 | 0.13 | 0.25 | 0.13 | 0.25 | 0.5 | 0.03 | 0.06 | 0.5 | 1 |
| *Providencia spp.* | 12012 | 0.25 | 0.25 | 0.5 | 0.5 | 1 | 0.5 | 0.13 | 0.13 | 0.5 | 1 |
| *Staphylococcus aureus* | 1756 | 0.02 | 0.06 | 0.25 | 0.13 | 0.25 | 0.06 | 0.06 | 0.03 | 0.06 | 0.03 |
| | 133 | 0.02 | 0.25 | 0.25 | 0.13 | 0.25 | 0.06 | 0.06 | 0.03 | 0.06 | 0.03 |
| *Enterococcus faecalis* | 27101 | 0.01 | 0.25 | 0.5 | 0.25 | 0.5 | 0.25 | 0.13 | 0.06 | 0.5 | 0.5 |
| | 9790 | 0.06 | 0.13 | 0.5 | 0.25 | 0.5 | 0.25 | 0.13 | 0.06 | 0.5 | 1 |
| *Pseudomonas aeruginosa* | Walter | 4 | 1 | 2 | 128 | 16 | 4 | 1 | 0.5 | 128 | 128 |

*)Reference compound: 7-(4-amino-1,3-dihydro-isoindol-2-yl)-1-cyclopropyl-6,8-difluoro-1,4-dihydro-4-oxo-3-quinoline-carboxylic acid (EP 343,560, Example 2)

EXAMPLE Z 1

5,7-Dihydro-6H-pyrrolo[3,4-b]pyridine

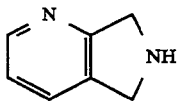

a) Ethyl N-propargylcarbamate 115 g (2.1 mol) of propargylamine is introduced into 1 l of toluene, 91 g of sodium hydroxide dissolved in 400 ml of water are added, and 239 g (2.2 mol) of ethyl chloroformate are added dropwise at 10° C. The mixture is stirred for three hours at room temperature, the organic phase is separated off, the aqueous phase is extracted using toluene, the organic solutions are dried over magnesium sulphate and concentrated, and the concentrate is distilled.

Yield: 221 g (83% of theory)
Boiling point: 101° C./20 mbar b) 2-(N-Ethoxycarbonyl-N-propargylaminomethyl)-pyrimidine 11.5 g (91 mmol) of ethyl N-propargylcarbamate are introduced into 90 ml of toluene, 20.3 g of KOH powder and 0.5 g of triethylbenzylammonium chloride are added, and 13.5 g (104 mmol) of 2-chloromethyl-pyrimidine (German Offenlegungsschrift 2,932,643) are added dropwise at room temperature. The mixture is stirred overnight at room temperature, the salts are filtered off with suction, the filtrate is washed using saturated sodium chloride solution, dried over magnesium sulphate and concentrated, and the concentrate is distilled.

Yield: 10.4 g (51% of theory)
Boiling point: 130° C./0.35 mbar c) Ethyl 5,7-dihydro-6H-pyrrolo[3,4-b]pyridine-6-carboxylate 7.7 g (35 mmol) of 2-(N-ethoxycarbonyl-N-propargyl-aminomethyl)-pyrimidine are refluxed for 40 hours in 150 ml of xylene. The mixture is concentrated, and the residue is recrystallised from ligroin.

Yield: 5.5 g (81.7% of theory)
Melting point: 77°–79° C.

d) 5,7-Dihydro-6H-pyrrolo[3,4-b]pyridine dihydrochloride 8.5 g (44 mmol) of ethyl 5,7-dihydro-1H-pyrrolo-[3,4-b]pyridine-6-carboxylate are refluxed overnight in 90 ml of concentrated hydrochloric acid. The solution is concentrated, the residue is stirred with acetone, and the salt is filtered off with suction and dried in the air.

Yield: 7.5 g (88% of theory)

EXAMPLE Z2

2,3-Dihydro-1H-pyrrolo[3,4-c]pyridine

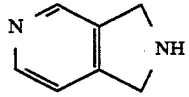

a) (N-Ethoxycarbonyl-N-propargyl)-aminomethylpyrazine 14 g (0.11 mol) of N-propargylurethane are introduced into 110 ml of toluene, 25 g of KOH powder and 0.5 g of triethylbenzylammonium chloride are added, and 24 g (22 mmol, 65%) of chloromethylpyrazine (J. Org. Chem. 38, 2049 (1973)) are added dropwise. The mixture is stirred overnight at room temperature, the salts are filtered off with suction, the filtrate is washed with sodium chloride solution, the organic phase is dried over potassium carbonate and concentrated, and the concentrate is distilled.

Yield: 10.5 g (44% of theory)
Boiling point: 126° C./0.4 mbar

Analysis by gas chromatography demonstrates that the product is 84% pure. In addition it contains 10% of ethyl 5,7-dihydro-6H-pyrrolo[3,4-b]pyridine-6-carboxylate and 6% of ethyl 2,3-dihydro-1H-pyrrolo[3,4-c]pyridine-2-carboxylate.

b) Ethyl 2,3-dihydro-1H-pyrrolo[3,4-c]pyridine-2-carboxylate 10.5 g of(N-ethoxycarbonyl-N-propargyl)aminomethylpyrazine are refluxed for 15 hours in 50 ml of trifluoroacetic acid. The batch is poured into water, the mixture is rendered alkaline using K₂CO₃ and extracted using methylene chloride, the organic solutions are dried over MgSO₄ and concentrated, and the concentrate is recrystallised from ligroin.

Yield: 6.3 g (67.8% of theory)
Melting point: 103° C.

According to analysis by gas chromatography, the product contains 6.8% of the isomeric ethyl 5,7-dihydro-6H-pyrrolo[3,4-b]pyridine-6-carboxylate.

The two isomers can be separated by chromatography on silica gel using ethyl acetate.

c) 2,3-Dihydro-1H-pyrrolo[3,4-c]pyridine 6 g (31.2 mmol) of ethyl 2,3-dihydro-1H-pyrrolo-[3,4-c]pyridine-2-carboxylate and 19.7 g (62.4 mmol) of Ba- (OH)₂. 8H₂O are refluxed for 15 hours in 100 ml of water. After cooling, the BaCO₃ is filtered off with suction, the filtrate is concentrated, and the residue is extracted by boiling five times with 50 ml portions of dioxane. The dioxane solutions are evaporated, and the residue is distilled.

Yield: 2.3 g
Boiling point: 73° C./0.18 mbar

According to ¹HNMR, the product contains 12% of 5,7-dihydro-6H-pyrrolo[3,4-b]pyridine.

d) 2,3-Dihydro-1H-pyrrolo[3,4-c]pyridine dihydrochloride 10.4 g (51 mmol) of ethyl 2,3-dihydro-1H-pyrrolo-[3,4-c]pyridine-2-carboxylate are refluxed for 15 hours together with 100 ml of concentrated hydrochloric acid. The batch is evaporated, and the crystalline residue is stirred with acetone. The product is filtered off with suction and dried in the air.

Yield: 9.8 g (100% of theory)

EXAMPLE Z3

5-Methyl-2,3,4,5,6,7-hexahydro-1H-pyrrolo[3,4-c]pyridine

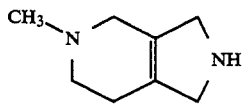

a) 2-Ethoxycarbonyl-5-methyl-2,3-dihydro-1H-pyrrolo-[3,4-c]pyridinium iodide 9.6 g (50 mmol) of ethyl 2,3-dihydro-1H-pyrrolo-[3,4-c]pyridine-2-carboxylate and 6.3 ml (100 mmol) of methyl iodide are refluxed for 15 hours in 50 ml of acetonitrile. The batch is poured into diethyl ether, and the salt which has precipitated is filtered off with suction and dried in the air.

Yield: 15.6 g (93% of theory)
Melting point: 137°-138° C.

b) Ethyl 5-methyl-2,3,4,5,6,7-hexahydro-1H-pyrrolo-[3,4-c]pyridine-2-carboxylate 15.3 g (45.8 mmol) of 2-ethoxycarbonyl-5-methyl-2,3-dihydro-1H-pyrrolo[3,4-c]pyridinium iodide are dissolved in 100 ml of absolute methanol, the solution is cooled to 0° C., and 7 g (0.1 mol) of sodium borohydride are added in 0.5 g portions. The mixture is subsequently stirred for 2 hours at room temperature, 100 ml of water are added, and the mixture is treated with K₂CO₃ and extracted with CHCl₃. The organic solutions are dried over K₂CO₃ and concentrated, and the residue is distilled.

Yield: 7 g (73% of theory)
Boiling point: 110° C./0.35 mbar c) 5-Methyl-2,3,4,5,6,7-hexahydro-1H-pyrrolo[3,4-c]-pyridine 6.3 g (30 mmol) of ethyl 5-methyl-2,3,4,5,6,7-hexahydro-1H-pyrrolo[3, 4-c]pyridine-2-carboxylate and 18.9 g (60 mmol) of Ba(OH)₂. 8H₂O are refluxed for 15 hours in 75 ml of water. After cooling, the BaCO₃ is filtered off with suction, the filtrate is concentrated, and the residue is extracted by boiling five times with 50 ml portions of dioxane. The dioxane solutions are concentrated, and the residue is distilled.

Yield: 2.1 g (46.6% of theory)
Boiling point: 95° C./10 mbar

EXAMPLE Z4

2-{N-Ethoxycarbonyl-N-propargyl-aminomethyl)-pyrimidine a) 2-Aminomethyl-pyrimidine 66.2 g (0.63 mole) of 2-cyano-pyrimidine (Liebigs Ann. Chem. 1981, 333) in 1.9 l of ethanol are hydrogenated in the presence of 130 ml of liquid ammonia and 5 g of Pd-C (5% Pd) at 20° C. and 5-10 bar of hydrogen. The catalyst is filtered off, the filtrate is concentrated and the residue is distilled.

Yield: 48.8 g (71% of theory)
Boiling point: 82 ° C./4 mbar b) 2-Ethoxycarbonylaminomethyl-pyrimidine 49.5 g (0.49 mol) of triethylamine are added to 49.5 g (0.45 mol) of 2-aminomethyl-pyrimidine in 450 ml of toluene and then 52 g (0.48 mol) of ethyl chlorocarbonic acid are added dropwise under cooling with ice. The mixture is subsequently stirred at room temperature for 2 hours. Triethylamine hydrochloride is filtered off with suction, the filtrate is washed with brine, dried with MgSO₄, concentrated, and distilled.

Yield: 63.3 g (77.6% of theory)
Boiling point: 126° C./0.09 mbar.

c) 2-(N-Ethoxycarbonyl-N-propargyl-aminomethyl)-pyrimidine 18.1 g (0.1 mol) of 2-ethoxycarbonylaminomethyl-pyrimidine are added to a suspension of 20 g (0.3 mol) of pulverized KOH and 1.1 g (5 mmol) of triethylbenzylammoniumbromide in 200 g of toluene, and then 18 g (0.12 mol) of propargylbromide (80% solution in toluene) at room temperature. The mixture is subsequently stirred for 15 hours at room temperature, the salts are filtered off with suction, the filtrate is washed with brine, dried with MgSO₄ concentrated and distilled. The reaction product is identical with that of example Z1b.

Yield: 18 g (86 % of theory)
Boiling point: 138° C./=.8 mbar

EXAMPLE 1

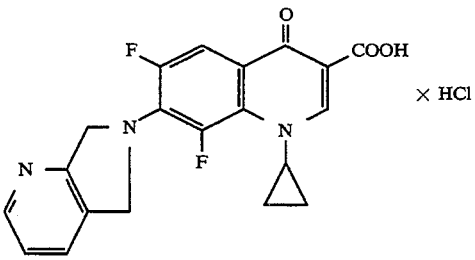

A. 1.45 g (5 mmol) of 1-cyclopropyl-6,7,8-trifluoro-1,4-dihydro-4-oxo-3-quinolinecarboxylic acid together with 560 mg (5 mmol) of 1,4-diazabicyclo-[2.2.2]octane and 630 mg (5.3 mmol) of 5,7-dihydro-6H-pyrrolo[3,4-b]pyridine are refluxed for 1 hour in a mixture of 10 ml of acetonitrile and 5 ml of dimethylformamide. The mixture is concentrated, the residue is stirred with water (pH=7), the solid which has precipitated is filtered off with suction and dried at 100° C. in vacuo.

Yield: 1.8 g of 1-cyclopropyl-7-(5,7-dihydro-6H-pyrrolo[3,4-b]pyridin-6-yl)-6, 8-difluoro-1,4-dihydro-4-oxo-3-quinolinecarboxylic acid B. 1.7 g (4.4 mmol) of the product from stage A are dissolved in 20 ml of half-concentrated hydrochloric acid, the solution is filtered, and the hydrochloride is precipitated by adding ethanol. The salt is filtered off with suction and dried in vacuo at 100° C.

Yield: 1.65 g (89% of theory) of 1-cyclopropyl-7-(5,7-dihydro-6H-pyrrolo[3, 4-b]pyridin-6-yl)-6,8-difluoro-1,4-dihydro-4-oxo-3-quinolinecarboxylic acid hydrochloride Melting point: 280°-290° C. (with decomposition)

EXAMPLE 2

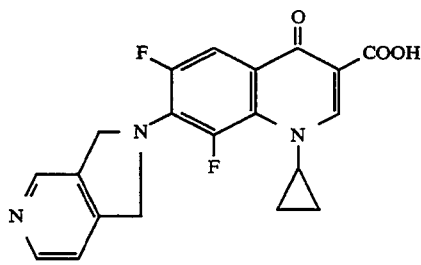

Analogousoly to Example 1A, the reaction is carried out with 2,3-dihydro-1H-pyrrolo[3,4-c]pyridine (86% pure, containing 12% of the isomeric 5,7-dihydro-6H-pyrrolo-3,4-b]pyridine) to give 1-cyclopropyl-7-(2,3-dihydro-1H-pyrrolo[3,4-c]pyridin-2-yl)-6,8-difluoro-1, 4-dihydro-4-oxo-3-quinolinecarboxylic acid, which is contaminated with approximately 10% of the isomeric product from Example 1A.

Melting points 246°-249° C. (with decomposition) (recrystallised from dimethylformamide)

EXAMPLE 3

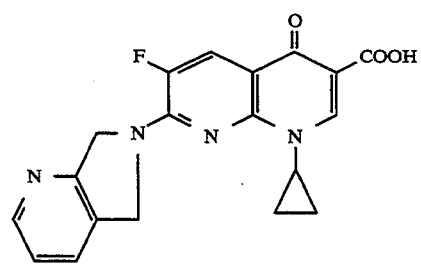

282 mg (1 mmol) of 7-chloro-1-cyclopropyl-6-fluoro-1, 4-dihydro-4-oxo-1,8-naphthyridine-3-carboxylic acid and 240 mg (2 mmol) of 5,7-dihydro-6H-pyrrolo[3,4-b]pyridine are stirred for 1 hour at room temperature in 3 ml of acetonitrile. The undissolved solid is filtered off with suction, washed with acetonitrile and water, and dried at 100° C. in a high vacuum.

Yield: 170 mg (46% of theory) of 1-cyclopropyl-(5,7-dihydro-6H-pyrrolo[3, 4-b]pyridin-6-yl)-6-fluoro-1,4-dihydro-4-oxo-1,8-naphthyridine-3-carboxylic acid Melting point: 275°-280° C. (with decomposition)

EXAMPLE 4

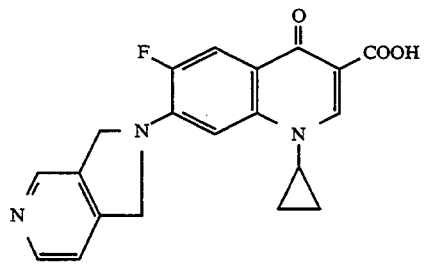

1.33 g (5 mmol) of 1-cyclopropyl-6,7-difluoro-1,4-dihydro-4-oxo-3-quinolinecarboxylic acid are refluxed for 5 hours in a mixture of 10 ml of acetonitrile and 5 ml of dimethylformamide in the presence of 1.8 g (1.6 mmol) of 1,4-diazabicyclo[2.2.2]octane and 1.7 g (9 mmol) of 2,3-dihydro-1H-pyrrolo[3,4-c]pyridine hydrochloride. The suspension is cooled, and the precipitate is filtered off with suction, washed with approx. 50 ml of water and dried in vacuo at 100° C.

Yield: 1.52 g ( 83% of theory) of 1-cyclopropyl-7-(2,3-dihydro-1H-pyrrolo[3, 4-c]pyridin-2-yl)-6-fluoro-1,4-dihydro-4-oxo-3-quinolinecarboxylic acid, Melting point: 297°-300° C. (with decomposition).

EXAMPLE 5

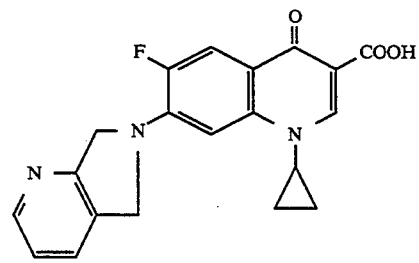

Analogously to Example 4, the reaction is carried out with 5,7-dihydro-6H-pyrrolo[3,4-b]pyridine hydrochloride to give 1-cyclopropyl-7-(5,7-dihydro-6H-pyrrolo[3,4-b]-pyridin-6-yl)-6-fluoro-1, 4-dihydro-4-oxo-3-quinolinecarboxylic acid of melting point 300°-304° C. (with decomposition).

EXAMPLE 6

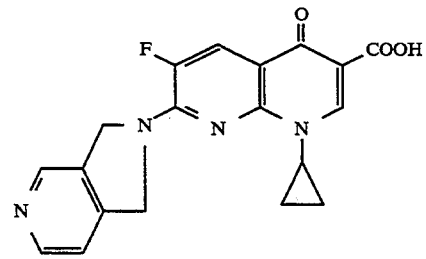

Analogously to Example 3, the reaction is carried out with 2,3-dihydro-1H-pyrrolo[3,4-c]pyridine (86%) to give 1-cyclopropyl-7-(2,3-dihydro-1H-pyrrolo[3,4-c]pyridin-2-yl)-6-fluoro-1, 4-dihydro-4-oxo-1,8-naphthyridine-3-carboxylic acid of melting point 275°-280° C. (with decomposition).

27

EXAMPLE 7

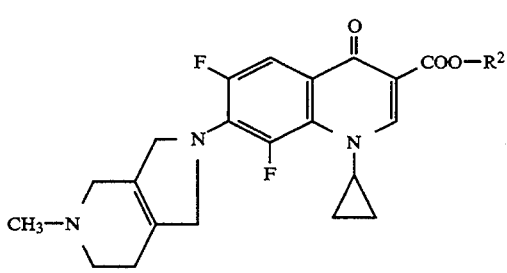

A. $R^2 = C_2H_5$
B. $R^2 = H \times HCl$
C. $R^2 = H$

A. A solution of 850 mg (2.7 mmol) of ethyl 1-cyclopropyl-6,7,8-trifluoro-1, 4-dihydro-4-oxo-3-quinolinecarboxylate in 5 ml of dimethylformamide and 10 ml of acetonitrile is refluxed for 7 hours with 370 mg (3.3 mmol) of 1,4-diazabicyclo[2.2.2]octane and 570 mg (3.8 mmol) of 5-methyl-2,3,4,5,6,7-hexahydro-1H-pyrrolo[3,4-c]pyridine. The mixture is evaporated, the residue is stirred with water, and the undissolved product is filtered off with suction, washed with water and dried in vacuo at 100° C.

Yield: 790 mg (68% of theory) of ethyl 1-cyclopropyl-6,8-difluoro-1, 4-dihydro-7-(5-methyl-2,3,4,5,6,7-hexahydro-1H-pyrrolo[3, 4-c]pyridin-2-yl)-4-oxo-3-quinolinecarboxylate Melting point: 163°-165° C. (with decomposition) (from glycol monomethyl ether)

B. 500 mg (1.2 mmol) of the product from stage A are refluxed for 2 hours in a mixture of 4 ml of glacial acetic acid and 3 ml of concentrated hydrochloric acid. The mixture is concentrated, the residue is stirred with ethanol, and the hydrochloride is filtered off with suction, washed with ethanol and dried in vacuo at 100° C.

Yield: 180 mg (35% of theory) of 1-cyclopropyl-6,8-difluoro-1,4-dihydro-7-(5-methyl-2, 3,4,5,6,7-hexahydro-1H-pyrrolo[3,4-c]-pyridin-2-yl)-4-oxo-3-quinolinecarboxylic acid hydrochloride Melting point: 274°-275° C. (with decomposition)

C. 850 mg (3 mmol) of 1-cyclopropyl-6,7,8-trifluoro-1, 4-dihydro-4-oxo-3-quinolinecarboxylic acid are reacted under the conditions of Example 19A.

Yield: 1 g ( 83% of theory) of 1-cyclopropyl-6,8-difluoro-1,4-dihydro-7-(5-methyl-2 3,4,5,6,7-hexahydro-1H-pyrrolo[3,4-c]-pyridin-2-yl)-4-oxo-3-quinolinecarboxylic acid Melting point: 210°-213° C. (with decomposition)

Dissolving this betaine in half-concentrated hydrochloric acid, evaporating the solution in vacuo and stirring the residue with ethanol gives the hydrochloride, which is identical to the product of Example 19B.

EXAMPLE 8

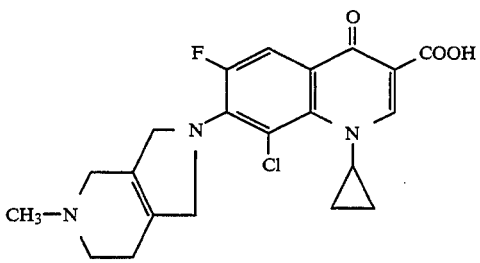

900 mg (3 mmol) of 8-chloro-1-cyclopropyl-6,7-difluoro-1, 4-dihydro-4-oxo-3-quinolinecarboxylic acid together with 370 mg (3.3 mmol) of 1,4-diazabicyclo[2.2.2]octane and 495 mg (3.3 mmol) of 5-methyl-2,3,4,5,6,7-hexahydro-1H-pyrrolo[3,4-c]pyridine are refluxed for 1 hour in a mixture of 10 ml of acetonitrile and 5 ml of dimethylformamide.

The suspension is cooled, and the precipitate is filtered off with suction, washed with water and dried in vacuo at 80° C.

Yield: 1 g (80% of theory) of 8-chloro-1-cyclopropyl-6-fluoro-1,4-dihydro-7-(5-methyl-2, 3,4,5,6,7-hexahydro-1H-pyrrolo[3,4-c]pyridin-2-yl)-4-oxo-3-quinolinecarboxylic acid Melting point: 215°-217° C. (with decomposition) (recrystallised from acetonitrile)

EXAMPLE 9

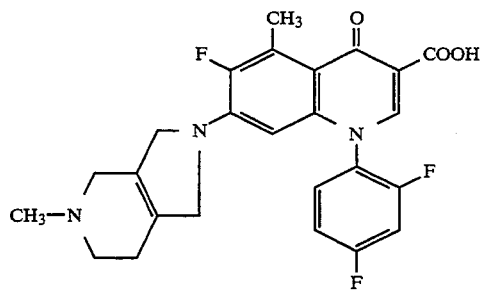

Analogously to Example 7A, the reaction is carried out with 1-(2,4-difluorophenyl)-6,7-difluoro-1,4-dihydro-5-methyl-4-oxo-3-quinolinecarboxylic acid to give 1-(2,4-difluorophenyl)-6-fluoro-1,4-dihydro-5-methyl-7-(5-methyl-2, 3,4,5,6,7-hexahydro-1H-pyrrolo[3,4-c]-pyridin-2-yl)-4-oxo-3-quinolinecarboxylic acid of melting point 270°-273° C. (with decomposition).

We claim:
1. A naphthyridone of the formula

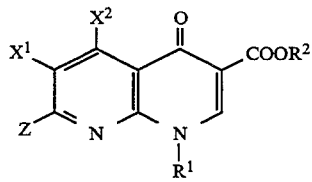

in which
$X^1$ represents halogen,
$X^2$ represents hydrogen, amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms, arylthio, halogen or methyl, $R^1$ represents alkyl having 1 to 4 carbon atoms, alkenyl having 2 to 4 carbon atoms, cycloalkyl having 3 to 6 carbon atoms, 2-hydroxyethyl, 2-fluoroethyl, methoxy, amino, methylamino, ethylamino, dimethylamino, or phenyl which is optionally substituted by 1 or 2 fluorine atoms, $R^2$ represents hydrogen, or represents alkyl which has 1 to 4 carbon atoms and which is optionally substituted by hydroxyl, methoxy, amino, methylamino or dimethylamino, or represents (5-methyl-2-oxo-1,3-dioxol-4-yl)-methyl, Z represents a radical of the structure

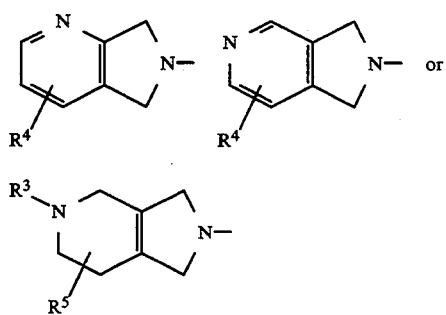

where $R^3$ represents hydrogen, optionally hydroxyl-substituted $C_1$–$C_3$alkyl, alkoxycarbonyl having 1 to 4 C atoms in the alkoxy moiety or $C_1$–$C_3$-acyl, $R^4$ represents hydrogen, hydroxyl,

hydroxymethyl or

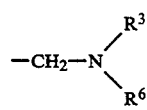

$R^5$ represents hydrogen, $C_1$–$C_3$-alkyl or cyclopropyl, and $R^6$ represents hydrogen or methyl, or a pharmaceutically acceptable hydrate, acid addition salt or alkali metal, alkaline earth metal, silver or guanidinium salt thereof.

2. A naphthyridone, hydrate or salt thereof according to claim 1, in which $X^1$ represents fluorine, $X^2$ represents hydrogen, amino, methylamino, hydroxyl, methoxy, fluorine, chlorine, bromine or methyl, $R^1$ represents alkyl having 1 to 3 carbon atoms, vinyl, cycloalkyl having 3 to 4 carbon atoms, 2-fluoroethyl, or phenyl which is optionally substituted by 1 or 2 fluorine atoms, $R^2$ represents hydrogen, or represents alkyl which has 1 to 2 carbon atoms and is optionally substituted by amino, methylamino or dimethylamino, or represents (5-methyl-2-oxo-1,3-dioxol-4-yl)-methyl, Z represents a radical of the structure

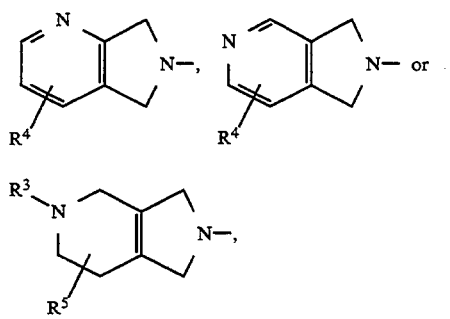

where $R^3$ represents hydrogen, optionally hydroxyl-substituted $C_1$–$C_2$-alkyl, alkoxycarbonyl having 1 to 4 C atoms in the alkoxy moiety or $C_1$–$C_3$-acyl, $R^4$ represents hydrogen, hydroxyl or

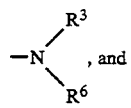

$R^5$ represents hydrogen or methyl.

3. A naphthyridone, hydrate or salt thereof according to claim 1, in which $X^1$ represents fluorine, $X^2$ represents hydrogen, amino, fluorine or bromine, $R^1$ represents alkyl having 1 to 2 carbon atoms, cyclopropyl, or phenyl which is optionally substituted by 1 or 2 fluorine atoms, $R^2$ represents hydrogen or alkyl having 1 to 2 carbon atoms, Z represents a radical of the structure

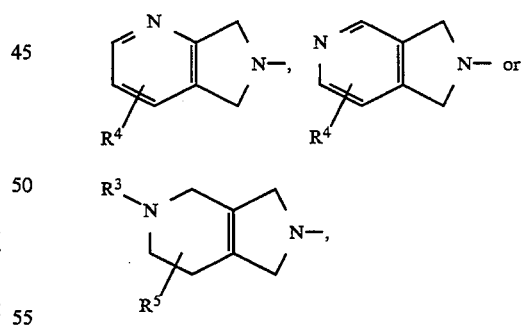

where $R^3$ represents hydrogen, methyl, alkoxycarbonyl having 1 to 4 C atoms in the alkoxy moiety, or $C_1$–$C_3$-acyl, $R^4$ represents hydrogen, hydroxyl or

$R^5$ represents hydrogen or methyl.

4. An antibacterial composition comprising an antibacterially effective amount of a compound or addition product thereof according to claim 1 and a diluent.

5. A composition according to claim 4 in the form of a tablet, capsule or ampule.

6. A composition according to claim 4, wherein the diluent comprises an animal feed stock.

7. A method of combating bacteria in a patient in need thereof which comprises administering to such patient an antibacterially effective amount of a compound or addition product thereof according to claim 1.

8. A method of promoting the growth of an animal which comprises administering to said animal a growth promoting effective mount of a compound or addition product thereof according to claim 1.

* * * * *